US006916452B1

(12) United States Patent
Rix et al.

(10) Patent No.: US 6,916,452 B1
(45) Date of Patent: Jul. 12, 2005

(54) STERILIZATION OF LIQUIDS USING ULTRA-VIOLET LIGHT

(75) Inventors: Eldred Rix, Kirstenhof (ZA); Attila Kurucz, Goodwood (ZA)

(73) Assignee: Hydrozone, Ltd.

( * ) Notice: Subject to any disclaimer, the term of this patent is extended or adjusted under 35 U.S.C. 154(b) by 23 days.

(21) Appl. No.: 10/110,448

(22) PCT Filed: Oct. 12, 2000

(86) PCT No.: PCT/ZA00/00189

§ 371 (c)(1),
(2), (4) Date: Aug. 12, 2002

(87) PCT Pub. No.: WO01/37675

PCT Pub. Date: May 31, 2001

(30)  Foreign Application Priority Data

Oct. 12, 1999  (ZA) ..................... 99/5540
Jan. 18, 2000  (ZA) ................. 2000/0188

(51) Int. Cl.[7] ............................... C02F 1/32
(52) U.S. Cl. .................. 422/186.3; 210/748; 250/438
(58) Field of Search ............................ 210/748, 198.1, 210/205; 422/24, 186.3; 250/432 R, 435, 250/436, 437, 438

(56)  References Cited

U.S. PATENT DOCUMENTS

| 2,340,890 | A | * | 2/1944 | Lang et al. ................. 250/429 |
| 2,636,991 | A | * | 4/1953 | Postell ...................... 250/436 |
| 3,182,193 | A |   | 5/1965 | Ellner et al. |
| 4,141,686 | A | * | 2/1979 | Lewis ........................ 250/436 |
| 4,534,282 | A |   | 8/1985 | Marinoza |
| 4,798,702 | A | * | 1/1989 | Tucker ......................... 422/24 |
| 5,709,799 | A | * | 1/1998 | Engelhard ................... 210/748 |
| 5,785,845 | A |   | 7/1998 | Colaiano |
| 6,280,615 | B1 | * | 8/2001 | Phillips et al. ........... 210/198.1 |

FOREIGN PATENT DOCUMENTS

| EP | 0 202 820 |   | 11/1986 |
| EP | 0470 518 A1 |   | 2/1992 |
| EP | 0686 601 |   | 12/1995 |
| FR | 1 278 161 |   | 10/1961 |
| FR | 1 310 471 |   | 10/1962 |
| GB | 639467 |   | 6/1950 |
| SU | 1159521 A | * | 6/1985 |
| SU | 1217315 A | * | 3/1986 |
| SU | 656297 | * | 12/1993 |

* cited by examiner

Primary Examiner—Frank M. Lawrence
(74) Attorney, Agent, or Firm—J. Wiley Horton

(57)  ABSTRACT

A sterilizer for milk and other liquids is disclosed, the sterilizer having an elongate outer housing (12) with a manifold (16) at each end. Dairy fittings (20) forming the inlet to and outlet from the sterilizer protrude from the manifolds (16).

3 Claims, 2 Drawing Sheets

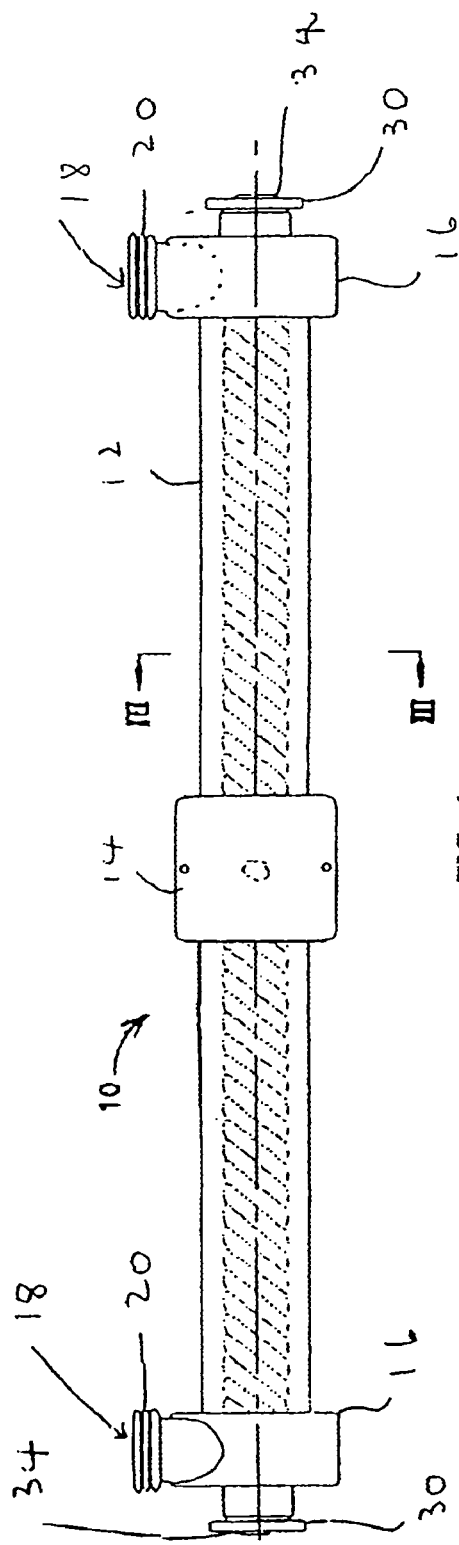
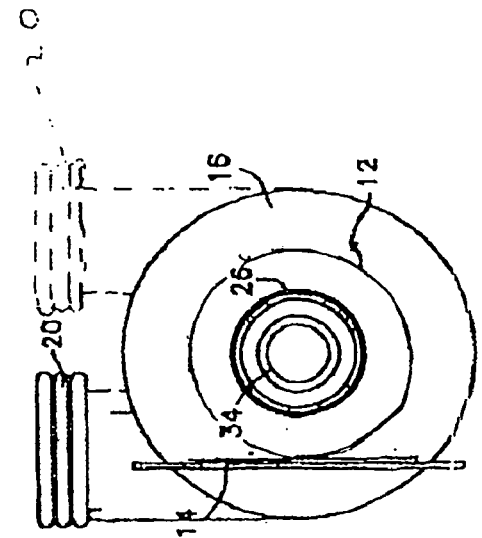
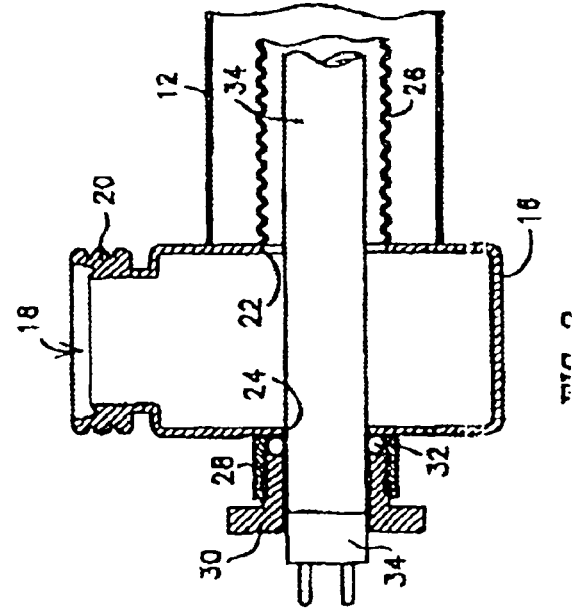
FIG 1
FIG 2
FIG 3

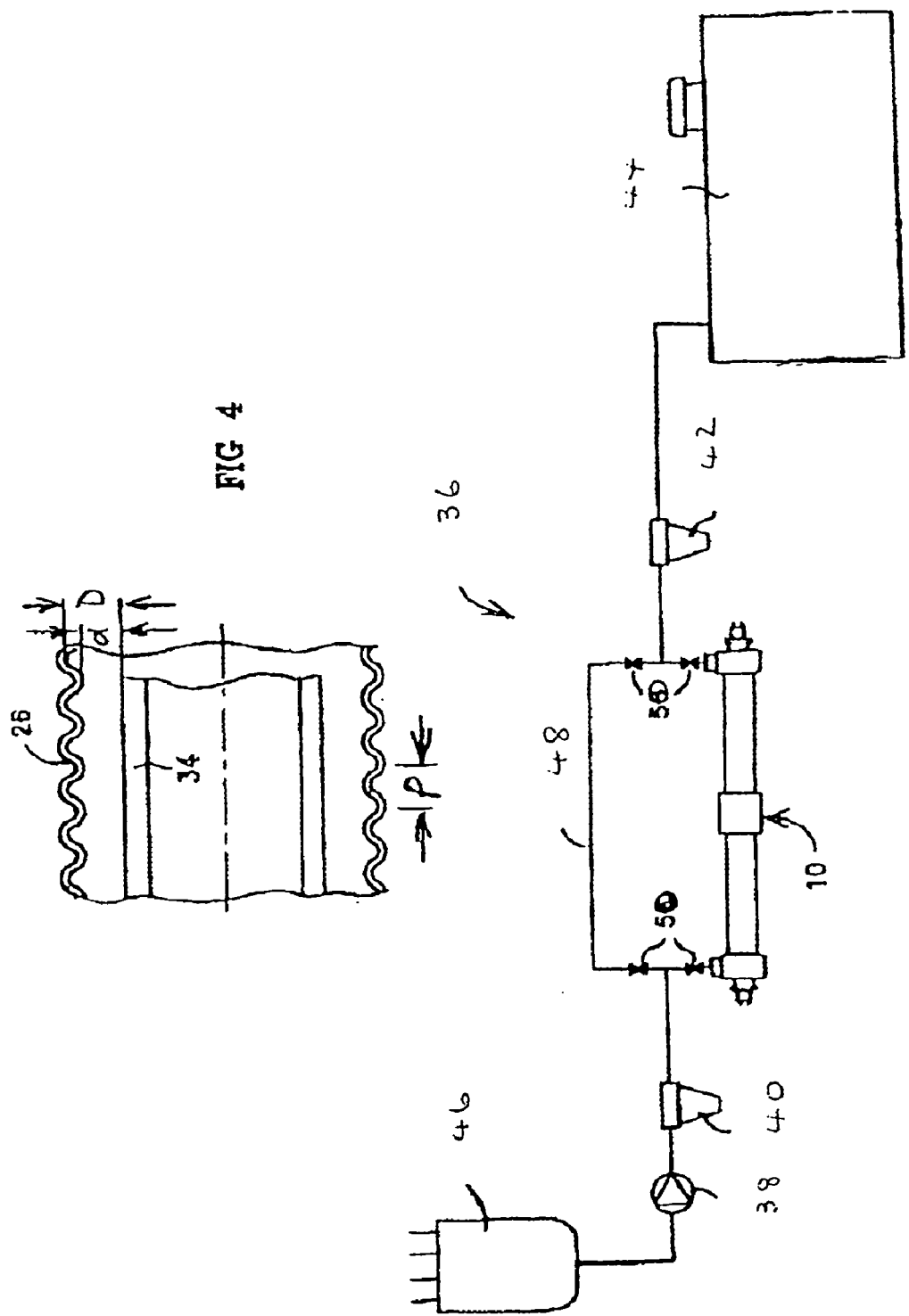

STERILIZATION OF LIQUIDS USING ULTRA-VIOLET LIGHT

FIELD OF THE INVENTION

THIS INVENTION relates to the sterilization of liquids using ultra-violet light.

The use in this specification of the term "sterilization" is meant to indicate a reduction in bacterial count in a liquid, and not necessarily a total elimination of bacteria.

BACKGROUND TO THE INVENTION

The use of ultraviolet (UV) light for the purpose of sterilizing a liquid is well known. A problem that arises with a turbid liquid is that the light does not penetrate very far into the liquid and hence liquid furthest from the UV lamp may not be sterilized at all or may not be properly sterilized.

South African patent specification 96/8029 discloses an elongate sterilizer in which a fluorescent tube is within, and co-axial with, an elongate housing. The sterilization chamber is between the fluorescent tube and the housing. The liquid inlet and liquid outlet are arranged tangentially with respect to the housing in an effort to cause the liquid to swirl and overcome the difficulty referred to above. It has been found, however, that the swirling motion imparted to the liquid as it enters the housing does not continue throughout the length of the housing, thus limiting the beneficial effect.

Other structures are known, such as that shown in U.S. Pat. No. 5,675,153, in which there is a helical vane in the space between the fluorescent tube and the housing, the vane extending from one end of the housing to the other. The vane is slotted and there is a gap between the vane and the inner surface of the housing. Such a structure would be completely unsuitable for the sterilization of milk, because of the many sharp corners where flow would stagnate and bacteria would be able to multiply.

There is a tendency for solids in milk to deposit on the surfaces defining the flow passage, in regions where there is insufficient flow velocity, so that the structure of U.S. Pat. No. 5,675,153 if it were to be used for the sterilization of milk, would suffer from deposits and as a consequence would require frequent cleaning. The structure would, in any event, be difficult to clean to the degree that is required in apparatus that is used for the handling of milk.

BRIEF DESCRIPTION OF THE INVENTION

According to one aspect of the invention there is provided a sterilizer for reducing the bacteria count in a liquid, the sterilizer comprising an elongate sheath, an elongate fluorescent tube extending along the sheath, there being a gap between the tube and the sheath through which gap the liquid to be sterilized flows, said sheath having an internal configuration including protuberances over which, in use, the liquid flows and which impart turbulence to the flowing liquid, and an inlet for the liquid which inlet is offset with respect to the sheath and the tube so as to cause the incoming liquid to swirl in the sheath.

In one form the sheath has a spiral groove in the inner face thereof with a spiral land between adjacent turns of the groove, the land forming said protuberances over which the liquid being sterilized flows. The shape of the protuberances is preferably such that they provide the inner surface of the sheath with a smoothly curved, undulating configuration. Preferably said tube and sheath are within and extend along an elongate outer housing.

According to a further aspect of the present invention there is provided a method of reducing the bacteria count in milk, the method comprising causing the milk to flow from a milking machine to a sterilizer in which the milk is subjected to ultraviolet radiation, the milk being subjected to said ultraviolet radiation before it cools to below 28° C.

The method can include the further step of cooling the milk down to storage temperature after subjecting it to ultraviolet radiation.

BRIEF DESCRIPTION OF THE DRAWINGS

For a better understanding of the present invention, and to show how the same may be carried into effect, reference will now be made, by way of example, to the accompanying drawings in which;—

FIG. 1 is a side elevation of a sterilizer in accordance with the present invention;

FIG. 2 is a longitudinal section through one end of the sterilizer, drawn to a larger scale;

FIG. 3 is a cross-section on line III—III of FIG. 1, drawn to the same larger scale;

FIG. 4 is a detail of part of FIG. 2; and

FIG. 5 is schematic diagram of a milk sterilization installation in accordance with the invention.

DETAILED DESCRIPTION OF THE DRAWINGS

Referring firstly to FIGS. 1 to 4, the sterilizer 10 illustrated is designed specifically for the purpose of sterilizing milk but can be used to sterilize not only turbid liquids but also transparent or translucent liquids. The sterilizer comprises an elongate stainless steel outer housing 12 which is circular in cross section. A mounting plate 14 is tack welded to the housing 12 midway between its ends (see FIG. 3). In another form the outer housing 12 is square in cross section.

At each end of the housing 12 there is an manifold 16, one manifold forming an inlet for milk to be sterilized, and the other manifold forming an outlet for sterilized milk. The manifolds 16 each have a port 18. The ports are each in a conventional mate dairy fitting 20 whereby a hose can be attached thereto. The fitting 20 of one manifold 16 is to one side of the vertical centre plane of the sterilizer (as shown in full lines in FIG. 3) and the fitting 20 of the other manifold 16 is to the other side of the centre plane as shown in dotted lines in FIG. 3.

Each manifold 16 has aligned openings 22, 24 in opposite walls thereof. The sterilizer further comprises a corrugated sheath 26 which is aligned with the opening 22 and extends the full length of the housing 12 between the manifolds 16.

Each manifold 16 has an internally threaded socket 28 secured thereto, the sockets 28 being aligned with the openings 24.

An externally threaded bush 30 is screwed into each socket 28 and there is a sealing ring 32 between each bush 30 and the wall of the manifold.

A fluorescent tube 34 (also referred to as a germicidal UV lamp) passes through the bushes 30, sockets 28, sealing rings 32, manifolds 16 and sheath 26, the ends of the fluorescent tube protruding from the bushes 30. When the bushes 30 are tightened the sealing rings 32 are compressed and grip the fluorescent tube 34, thereby forming liquid-tight seals.

The sheath 26 is of stainless steel and is formed with a helically extending corrugation. As can best be seen in FIG. 4, the helical corrugation has a pitch P of about 6 mm and provides the inside of the tube with a smoothly curved undulating surface when the tube is viewed in radial cross section, without any sharp corners or discontinuities where flow stagnation can occur.

The sheath 26 has a nominal diameter of about 40 mm. Being of stainless steel, the inner surface of the sheath 26 is reflective. The radial gap between the fluorescent tube 34 and the sheath 26 varies between about 5 mm at the troughs of the corrugations (the distance d) to about 7 mm at the crests (the distance D).

In another form the sheath 26 has a spiral groove extending along the inner face thereof with a spiral land separating adjacent turns of the groove. The gap between the land and the outer face of the tube 34 is approximately 5 mm.

Milk flowing through the sterilizer 10 passes through the narrow annular gap between the fluorescent tube 34 and the corrugated sheath 26. As the milk flows into the sterilizer a swirling motion is imparted to it, and hence turbulence is introduced, by the tangential position of the inlet fitting 20. The corrugations maintain, throughout the length of the sterilizer, the turbulence introduced into the milk as it flows into the manifold. This ensures that all the milk is subjected to UV light. The tangential arrangement of the outlet fitting 20 ensures that the milk flows smoothly out of the sterilizer without the fitting causing a back pressure which could dampen the turbulent flow.

If the inlet manifold and fitting do not impart turbulence to the incoming liquid, then the surface of the sheath breaks up the smooth flow of the incoming liquid and introduces turbulence.

It has been found that the best results are obtained when the velocity of the milk flowing through the gap between the fluorescent tube 34 and the sheath 26 is about 3 m/s, preferably between 3 and 3.5 m/s. At lower flow velocities there is a fall off in the turbulence that is required to ensure a proper irradiation of all the milk. At higher flow velocities, there is a tendency for butter formation to take place. There is also at higher velocity a tendency for the tube 34 to be coated thereby blocking off UV light.

Referring now to FIG. 5, reference numeral 36 generally indicates an installation for sterilizing milk, the installation being erected on a dairy farm and including a sterilizer 10 of the type described above with reference to FIGS. 1 to 4.

The installation 36 comprises a pump 38, a first filter 40 connected upstream of the sterilizer 10, a second filter 42 connected downstream of the sterilizer 10, and a bulk cooler tank 44. The pump 38 has its suction inlet connected to the milk collecting bowl 46 of a milking machine, and pumps the milk from the milk collecting bowl to the bulk cooler tank 44 via the first filter 40, the sterilizer 10 and the second filter 42. Cooling of the milk takes place in the tank 44.

The installation 36 includes a bypass line 48 bypassing the sterilizer 10. Bypass valves 50 are provided to divert flow from the sterilizer 10 to the bypass line and to isolate the sterilizer. If desired, the bypass line 48 may be substituted by a second sterilizer 10 so that flow can be diverted from one sterilizer to the other.

The filter 40 is provided to filter out hair and other dirt from the milk that is received from the milk collecting bowl. The second filter 42 is provided as a safety feature, to prevent glass fragments or other parts of the fluorescent tube 34 from finding their way into the tank 44 in the event of a breakage.

Two or more sterilizers 10 can be provided in series.

It is an important feature of the invention that the milk is subjected to ultraviolet radiation in the sterilizer 10 while the milk is still warm. The fatty constituents of milk start to separate from the rest of the milk when the temperature falls below 28° C. This is referred to as "crystallization". By passing the milk through the sterilizer while the milk is still at a temperature of 28° C. or above the tendency of the fatty constituents to collect on the inside surfaces of the sterilizer is minimized. Thus sterilization occurs before the milk cools to below 28° C.

While the use of the sterilizer 10 to irradiate milk has been described above it is to be understood that the sterilizer could also be used to sterilize other liquids. For example, it could be used to sterilize liquids such as wine and petroleum.

What is claimed is:

1. A sterilizer for reducing the bacteria count in a liquid, comprising:
   a. an elongate sheath, having a first end, a second end, and a central axis;
   b. an elongate fluorescent tube extending along said sheath, there being a gap between said tube and said sheath through which said liquid flows;
   c. wherein said sheath has a surface facing toward said fluorescent tube, wherein said surface includes protuberances over which, in use, said liquid flows, thereby imparting turbulence to said flowing liquid;
   d. wherein said surface facing toward said fluorescent tube has a smoothly curved spiral groove with a smoothly curved spiral land between adjacent turns of said smoothly curved spiral groove, with said smoothly curved groove and said smoothly curved land forming said protuberances over which said liquid flows;
   e. an inlet manifold, connected to said first end of said elongate sheet; and
   f. said inlet manifold including an inlet port for said liquid, wherein said inlet port is offset from said central axis of said elongate sheet in order to impart rotational flow to said liquid as said liquid flows into said first end of said elongate sheath.

2. A sterilizer as claimed in claim 1, wherein said tube and said sheath are within and extend along an elongate outer housing.

3. A sterilizer as claimed in claim 1, further comprising an inlet which is offset with respect to said sheath and said tube so as to cause said liquid to swirl as it flows into said sheath, an outlet manifold, connected to said second end of said elongate sheath, with said outlet manifold including an outlet port for said liquid, wherein said outlet port is offset from said central axis of said elongate sheath in order to maintain said rotational flow of said liquid as said liquid flows into said second end of said elongate sheath.

* * * * *